United States Patent [19]

Saad

[11] Patent Number: 5,727,553
[45] Date of Patent: Mar. 17, 1998

[54] CATHETER WITH INTEGRAL ELECTROMAGNETIC LOCATION IDENTIFICATION DEVICE

[76] Inventor: Saad A. Saad, 3 Kimball Turn, Holmdel, N.J. 07733

[21] Appl. No.: 626,993
[22] Filed: Apr. 3, 1996

Related U.S. Application Data

[63] Continuation-in-part of Ser. No. 621,568, Mar. 25, 1996, abandoned.

[51] Int. Cl.$^6$ .................................................. A61B 6/12
[52] U.S. Cl. .................... 128/653.1; 128/899; 128/737; 324/219; 324/234
[58] Field of Search .......................... 128/653.1, 899, 128/737, 654, 656, 657, 658, 897; 324/219, 234, 239, 220, 207.11

[56] References Cited

U.S. PATENT DOCUMENTS

| | | | |
|---|---|---|---|
| 3,622,784 | 11/1971 | Del Guercio | 250/71.5 R |
| 3,631,848 | 1/1972 | Muller | 128/2.05 R |
| 3,659,588 | 5/1972 | Kahn | 128/2 R |
| 4,173,228 | 11/1979 | Van Steenwyk et al. | 128/653 |
| 4,327,722 | 5/1982 | Groshong et al. | 128/214.4 |
| 4,416,289 | 11/1983 | Bresler | 128/737 |
| 4,431,005 | 2/1984 | McCormick | 128/656 |
| 4,432,369 | 2/1984 | Halvorsen | 128/653 |
| 4,445,501 | 5/1984 | Bresler | 128/1.5 |
| 4,572,198 | 2/1986 | Codrington | 128/653 |
| 4,880,414 | 11/1989 | Whipple | 604/283 |
| 4,905,698 | 3/1990 | Strohl, Jr. et al. | 128/653 R |
| 4,963,133 | 10/1990 | Whipple | 604/283 |
| 4,976,261 | 12/1990 | Gluck et al. | 128/207.15 |

OTHER PUBLICATIONS

"Catheter Placement Without Fluoroscopy", sales brochure for Fluoro-Free® Implantable Access Systems and Cath-Finder® Catheter Tracking System; 2 pages, SIMS Deltec, Inc. (May 1995).

"Now You See It. Now You Don't", sales brochure for P.A.S. Port® and Port-A-Cath® II Fluoro-Free® systems; 4 pages, SIMS Deltec, Inc. (May 1995).

"P.A.S. Port® Fluoro-Free® Implantable Peripheral Access System", sales brochure, 1 page, Pharmacia Deltec Inc. (1994).

Hickman®, Broviac® and Leonard™ Vascular Access Catheters, Instructions for Use, pp. 1-20, Davol® Inc. Subsidiary of C.R. Bard, Inc. (Mar. 1988).

BardPort™ Implanted Ports With Groshong® Catheters Instruction for use, pp. 1-37, Bard® Access Systems (Nov. 1994).

Port-A-Cath® Fluoro-Free® Vascular Access Systems, Instructions For Use, pp. 1-34, SIMS Deltec, Inc. (1995).

*Primary Examiner*—Marvin M. Lateef
*Assistant Examiner*—Eleni Mantis Mercader
*Attorney, Agent, or Firm*—Michaelson & Wallace; Michael P. Straub; Peter L. Michaelson

[57] ABSTRACT

Catheters incorporating an electromagnetic field detection device for use in conjunction with a catheter locating apparatus to determine the position of a catheter without the use of X-rays is disclosed. The electromagnetic field detection device includes a pair of leads incorporated into the wall of the catheter and a coil of fine wire located at the distal end of the catheter. In a closed end catheter embodiment, a core of magnetically permeable material is located inside the coil. In an open ended catheter embodiment the core is either omitted or a hollow core is used. In a Venous catheter embodiment, one way valves are located in the sidewall of the catheter near the catheter's distal end. The one way valves permit the injection of fluid into tissue through the catheter while preventing blood from flowing into the catheter. The incorporation of the electromagnetic field detection device directly into the catheter of the present invention permits continuous and/or periodic catheter location monitoring to be performed without the use of X-rays. Furthermore, the flexibility problems and risk of breaking the guide wire attached to the known removable detector device is avoided. In various embodiments, a radio-opaque strip is incorporated into the catheters of the present invention permitting a permanent record of the catheters position to be made and placed in a patients file using conventional X-rays.

17 Claims, 6 Drawing Sheets

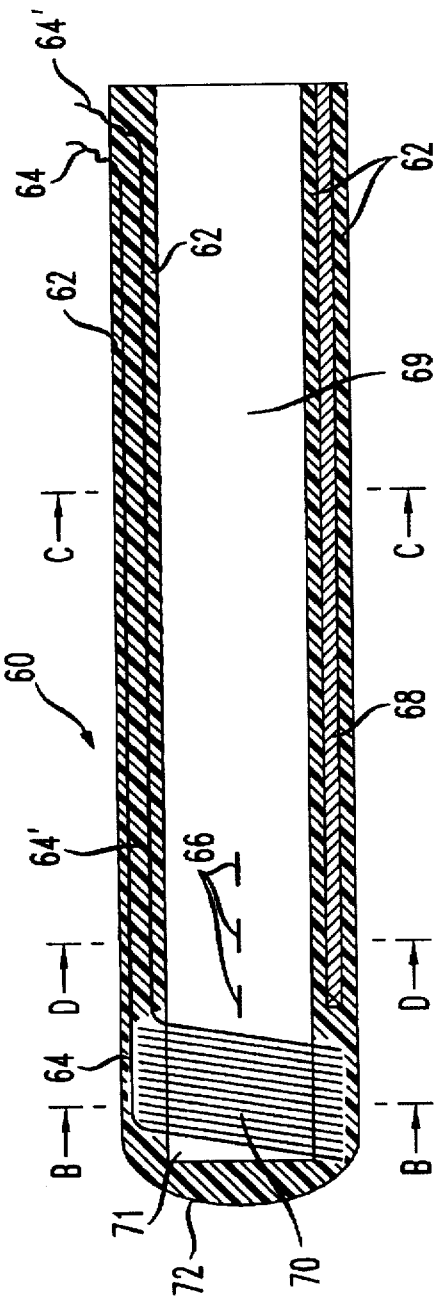
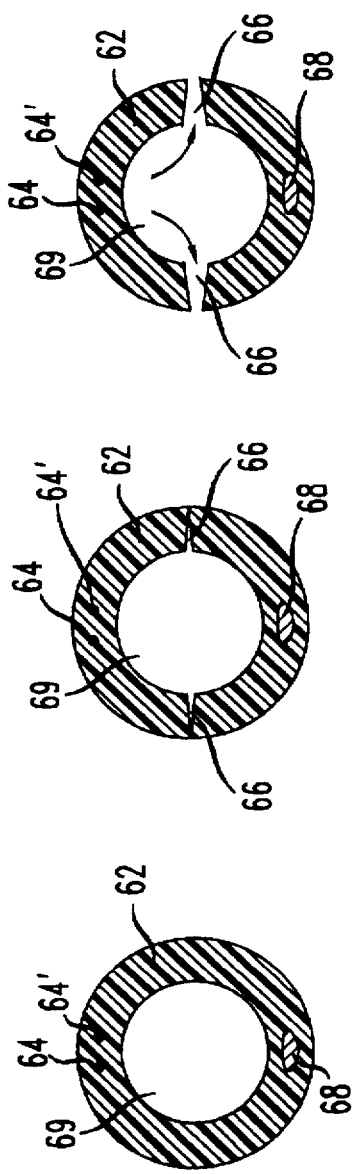
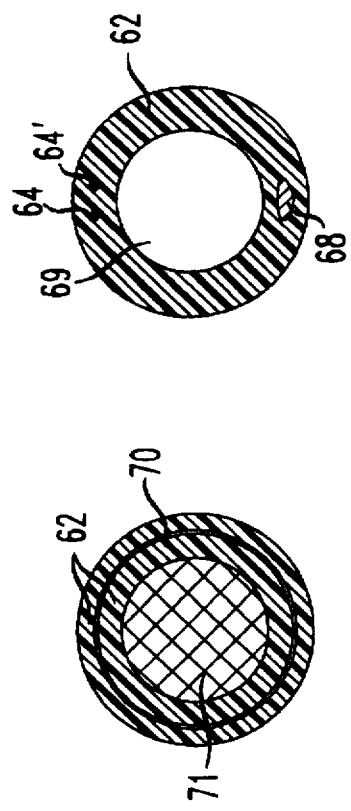

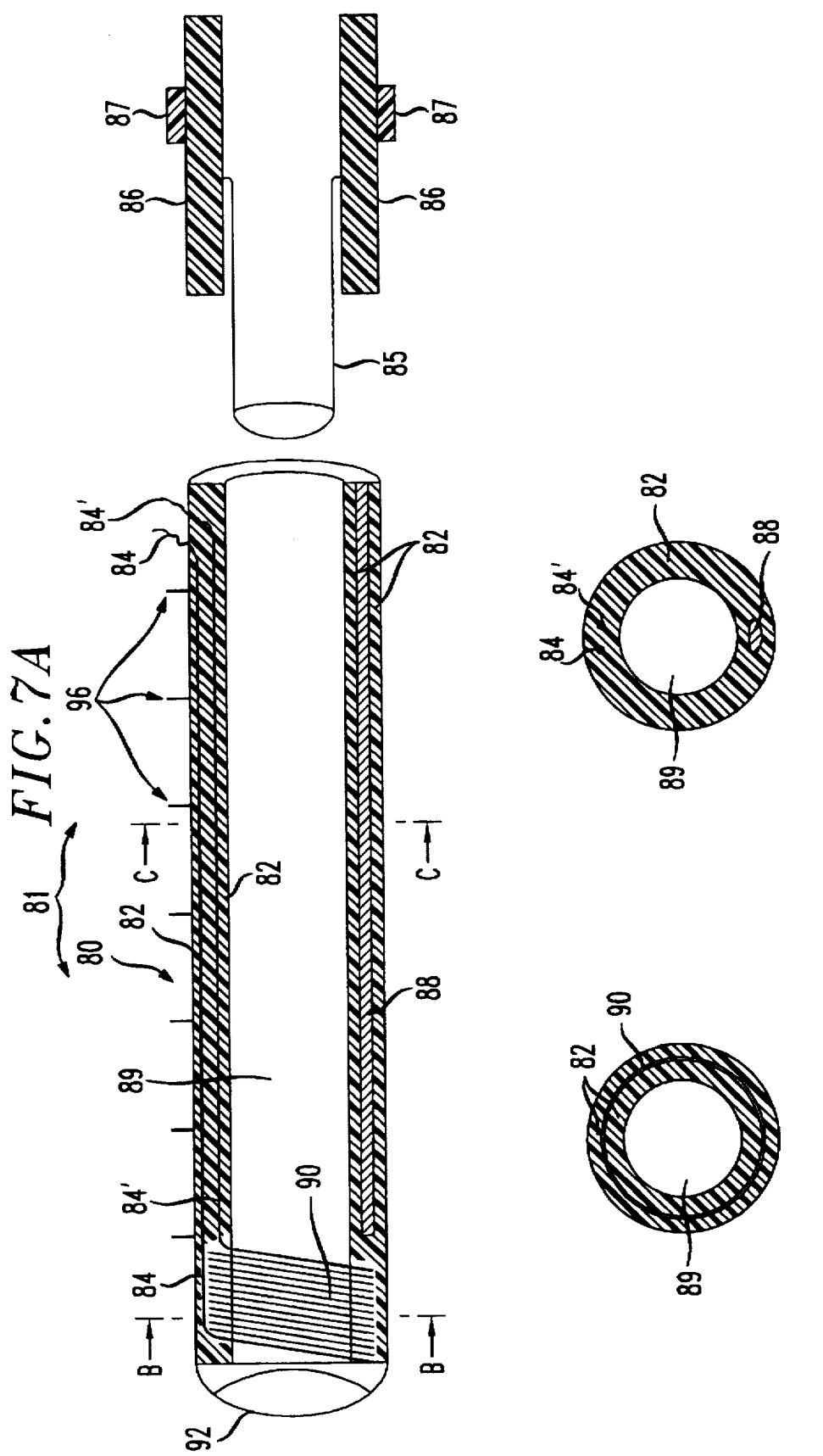

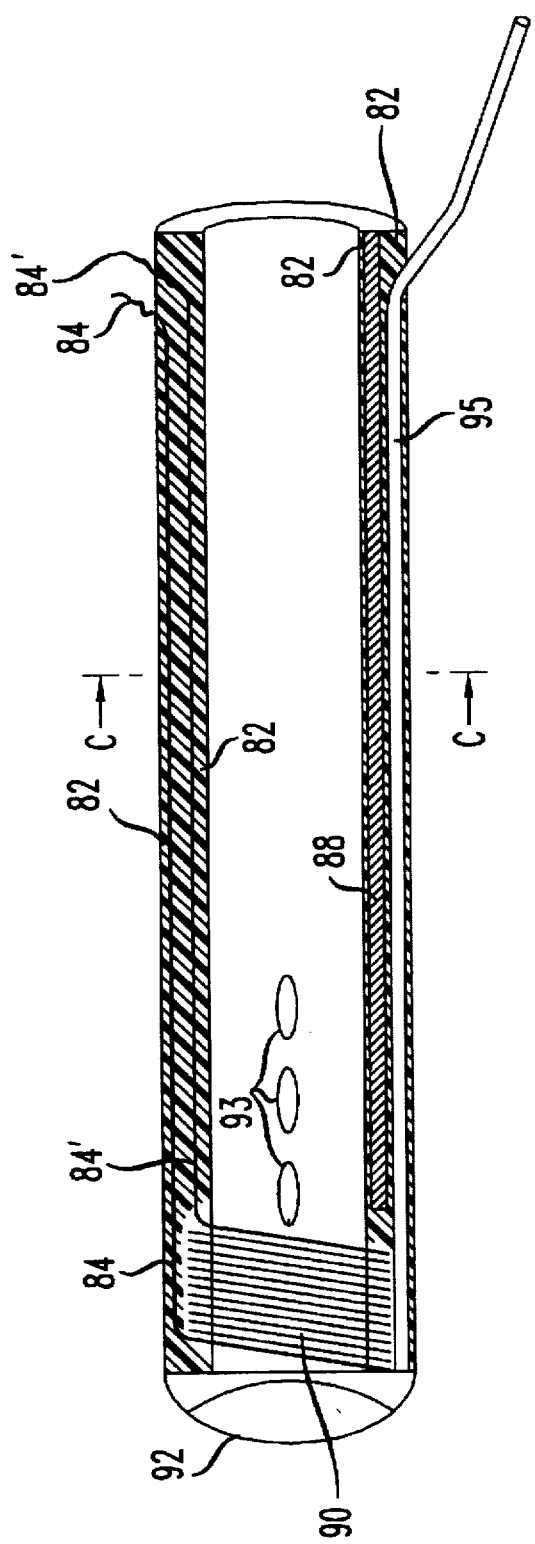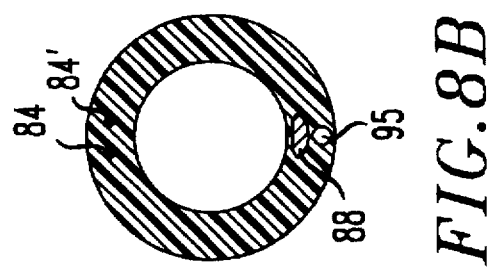

CATHETER WITH INTEGRAL ELECTROMAGNETIC LOCATION IDENTIFICATION DEVICE

RELATED APPLICATIONS

This application is a continuation-in-part of now abandoned U.S. patent application Ser. No. 08/621,568, filed on Mar. 25, 1996, entitled "IMPROVED CATHETER WITH INTEGRAL ELECTROMAGNETIC LOCATION IDENTIFICATION DEVICE" of which Dr. Saad Saad is the sole inventor.

FIELD OF THE INVENTION

The present invention is directed to catheters and, more particularly, to catheters which include a locating device.

BACKGROUND OF THE INVENTION

Catheters are frequently used in medical procedures for the injection or withdrawal of fluids from, e.g., biological tissue. During many procedures, the proper location of the tip of a catheter is of critical importance.

Known catheters may be grouped according to the type of tip, i.e., distal end, the catheters have. There are generally two types, open end catheters where the distal end of the catheter is open and closed end catheters where the distal end of the catheter is sealed. Open end catheters include, e.g., arterial catheters, gastrointestinal catheters, Broviac catheters, and Mickman catheters. These catheters may be vented, e.g., as in the case of the gastrointestinal catheters, or unvented as in the case of the arterial catheters. Closed end catheters may be used for, e.g., injecting fluid into veins. Closed end catheters frequently include slits in the side wall of the catheter as opposed to the end of the catheter.

Referring now to FIG. 1A, there is illustrated a known open ended catheter generally indicated by the reference numeral 10. A cross section of the known catheter 10 at location B, is illustrated in FIG. 1B. As illustrated, the catheter 10 includes a tubular catheter wall 13 which incorporates a radio-opaque material 12. A strip of the radio-opaque material 12 extends down the length of the catheter 10 as illustrated in FIG. 1A. The distal end of the known catheter 10 includes an opening 14 through which fluids can be injected or withdrawn from biological tissue into which the catheter 10 is inserted.

Referring now to FIG. 2, there is illustrated a known closed end catheter, i.e., a Venous catheter, generally indicated by the reference numeral 20. The known Venous catheter 20 includes a plurality of one way valves 26, a radio-opaque strip 22, and a sealed distal end with a rounded tip 24. The one way valves 26 permit fluid to be injected into a vein while preventing backflow of blood into the catheter 20. By using the one way valves 26 the need to use a drug, e.g., Heparin, to prevent blood from clotting in the catheter as a result of the flow of blood into the catheter's openings is avoided.

To facilitate catheter placement and to monitor the location of a catheter, e.g., within the human body, a plurality of catheter location detection and monitoring methods and devices have been employed. The most common of these techniques requires the use of X-rays.

The X-ray location method commonly in use today is referred to as Fluoroscopy. Such a catheter locating procedure has several disadvantages. First, it results in the patient and person performing the X-ray procedure being exposed to X-rays with their harmful consequences. Second, it is costly to perform in terms of equipment costs and the cost of having a highly trained person read and interpret the X-ray results. Third, by the time the X-ray is taken, developed, and interpreted, the position of the catheter may have shifted. Accordingly, multiple X-rays may be required to determine the location of the catheter over a period of time. Fourth, because of the relatively large size of X-ray equipment, it is not readily available during patient transport and in field locations where, e.g., emergency treatment may be required.

As an alternative to X-ray location detection methods, nuclear magnetic resonance (NMR) imaging as described in U.S. Pat. No. 4,572,198 has been used to determine the location of a catheter designed for use with an NMR imaging system. Referring now to FIG. 3A there is illustrated an open ended catheter 29 intended for use with an NMR imaging system. The catheter 29 includes a sheath 30, which has embedded in the wall thereof a pair of conductors 32 and 32' which are formed of a foil composite obtained by, e.g., plating conductive materials of selected magnetic susceptibility to yield a composite of desired susceptibility substantially matching that of the sheath 30. As illustrated in FIG. 3B, the tip 34 of the catheter contains a loop 36 connecting the conductors 32 and 32'. When excited by a weak pulse source, the loop supports a dipole magnetic field which locally distorts the NMR image providing an image cursor on the magnetic resonance imaging display. The U.S. Pat. No. 4,572,198 teaches that it is preferable that the excitation be weak so that the cursor will be minimal in extent.

The NMR imaging catheter locating system has the significant disadvantage of requiring large, expensive NMR imaging equipment which is not available at many hospitals. In addition to the size and cost of the NMR imaging equipment, the catheter used with the system is relatively difficult to construct given the use of foil conductors formed by plating or other deposition techniques and the requirement that the resulting conductors have a magnetic susceptibility substantially matching that of the sheath 30.

Another method of locating a catheter is described in U.S. Pat. No. 4,431,005. The open ended catheter described in the U.S. Pat. No. 4,431,005 patent is illustrated in FIG. 4. As illustrated the known open ended catheter 38 includes a band of foil 39 located near the tip of the catheter 38. The band of foil is made from a magnetically permeable metal. The location of the band of foil, and thus the tip of the catheter, is detected using a detecting instrument and a probe located external to the tissue in which the tip of the catheter 38 is placed. The probe generates a small magnetic field. The probe is used to scan the tissue into which the catheter was inserted, until the detecting instrument detects a disturbance in the probe's magnetic field indicative of the location of the metal band.

While the catheter locating system described in U.S. Pat. No. 4,445,501 avoids the need to use X-rays to locate the tip of the catheter, it has failed to gain widespread acceptance. This suggests that the described catheter and/or locating system suffers from one or more deficiencies. Accordingly, there is still a need for a catheter and catheter locating system which avoids the use of X-rays.

Referring now to FIG. 5, another known open ended catheter 50 and a removable detector 52 is illustrated. The removable detector 52 acts as an electromagnetic field detector. The illustrated catheter 50 and removable detector 52 are used with a catheter locating system as described in U.S. Pat. No. 4,905,698. The removable detector 52 is located in the tip of a hollow cable jacket or guidewire 53, and includes a generally cylindrical core 54 formed of a magnetically permeable material. The core 54 includes a coil 58 of fine wire wound thereon coaxial with the guidewire 59. The coil 58 contains leads 59 which extend through the hollow interior of the guidewire to a controller.

During operation, a catheter locating device which generates a electromagnetic field in response to alternating current signals is passed over the tissue into which the catheter 50 and removable detector 52 are inserted. The coil 58 generates an output voltage when the catheter locating device is placed in proximity to the coil 58. The catheter locating device is external to the tissue in which the catheter 50 is located. Accordingly, its position can be visually observed.

The position of the coil 58 and thus the tip of the catheter 50, relative to the location of the catheter locating device, is determined as a function of the output voltage generated by the coil 58. When the catheter locating device and the coil 58 are in close proximity to each other an indicator light is illuminated. The indicator light in combination with the physical position of the catheter locating device provide a visual indication of the position of the tip of the catheter 50.

The catheter locating apparatus described in U.S. Pat. No. 4,905,698 offers several advantages over the prior art systems discussed above. It eliminates the need for the use of relatively large and expensive equipment e.g., X-ray or NMR imaging equipment. Furthermore, the system requires relatively little training to use and, because of its small size offers a good degree of portability. As a result of these features, catheter locating apparatus which are the same as or similar to the one described in U.S. Pat. No. 4,905,698 have achieved some degree of acceptance for applications involving open ended catheters where the catheter undergoes relatively little bending during insertion, e.g., central Venous line insertion.

Despite the advantages of the above described catheter locating system, the known system still has many disadvantages which need to be overcome.

After the catheter 50 is inserted and its position detected using the removable detector 52, the detector 52 is normally removed to provide space for the injection or withdrawal of, e.g., fluids, through the catheter 50. Once the detector 52 is removed, the position of the catheter 50 can no longer be monitored using the catheter locating device. The position of the catheter may change during the process of removing the detector 52 or at any time thereafter. Furthermore, reinsertion of the removable detector 52 is generally not practical because of the problem of kinking of the guidewire attached to the detector.

Normally the known catheter 50 is inserted with the removable detector 52 located inside the catheter 50. The presence of the removable detector 52 increases the rigidity of the catheter assembly making it less flexible than a catheter which does not have the detector inserted therein. The increased rigidity of the combined catheter/detector assembly make it unsuitable for applications, e.g., an arterial catheter, where the catheter undergoes a great deal of flexing during insertion.

The known catheter locating system with the removable detector 52 is also unsuitable for applications where, upon insertion, the catheter assumes a relatively curved shape. Curves in the catheter 50, make it difficult to remove the detector 52 and result in an increased risk of breaking the guide wire attached to the detector during the removal process. The risk of breaking the guide wire attached to the detector during removal of the detector 52 is an unfortunate drawback to the use of the known catheter and catheter locating system.

Another disadvantage of the known catheter locating system is that it fails to provide a permanent record of indicating a catheter's location which can be placed in, e.g., a patient's medical file.

Another disadvantage of the known catheter locating system is that the catheter is an open-ended catheter. The blood can go back to the catheter lumen and may clot inside the catheter. Such an occurrence requires the removal of the known catheter. To prevent blood clotting there is a need to use a drug such as Heparin. Heparin is expensive and has many disadvantages for example, biological tissue bleeding in the brain, gastrointestinal track and subcutaneous tissue.

Accordingly, there is a need for an improved catheter and catheter locating method which permits for the continuous or periodic monitoring of a catheter's location without the use of harmful X-rays. It is also desirable that a catheter used with such a system be flexible enough to be used for a variety of purposes. In addition the improved catheter design should be applicable to both open ended and closed ended catheters. The ability to make a permanent record of a catheters location is also a desirable feature.

SUMMARY OF THE PRESENT INVENTION

The present invention is directed to catheters which include a device to assist in detecting the location of the catheter.

As will be described below, in accordance with the present invention an electromagnetic field detector device is incorporated directly into a catheter. In this manner, the detector device becomes an integral part of the catheter of the present invention.

The incorporation of the detector device into the catheter makes the catheter suitable for use with a catheter locating apparatus which is the same as or similar to that described in U.S. Pat. No. 4,905,698. Using such a catheter locating apparatus the location of the catheter 60 may be determined without the use of X-rays.

Because the catheter design of the present invention, provides for the permanent presence of a detector device within the catheter of the present invention, the location of the catheter can be monitored at any time without the need for harmful X-rays. This is a significant advantage over the prior art system which uses a removable detector.

In addition to permitting the continuous or periodic monitoring of catheter location, the incorporation of the detector device directly into the catheter of the present invention overcomes many of the problems associated with the use of a removable detector device.

As will be discussed below, the catheter of the present invention will generally be more flexible than a catheter assembly incorporating a removable detector. This permits the catheter of the present invention to be used for a variety of applications which the known catheter and removable detector are unsuitable for. In addition, since the detector device is incorporated into the catheter the problems associated with removing the known removable detector device from a catheter, e.g., the possible breaking of the guide wire attached to the detector, is avoided altogether.

The above described features and advantages of the present invention along with others are discussed in detail below.

BRIEF DESCRIPTION OF THE DRAWINGS

FIG. 6A illustrates a catheter, suitable for use as a Venous catheter, implemented in accordance with a first exemplary embodiment of the present invention.

FIGS. 6B through 6E illustrate cross sectional views of the exemplary catheter illustrated in FIG. 6A.

FIG. 7A illustrates a catheter device including an open ended catheter implemented in accordance with the present invention.

FIGS. 7B and 7C illustrate cross sectional views of the catheter illustrated in FIG. 7A.

FIG. 8A illustrates a closed end catheter incorporating a vent tube implemented in accordance with an exemplary embodiment of the present invention.

FIG. 8B illustrates a cross section of the catheter of FIG. 8A.

DETAILED DESCRIPTION

Figure 1A:
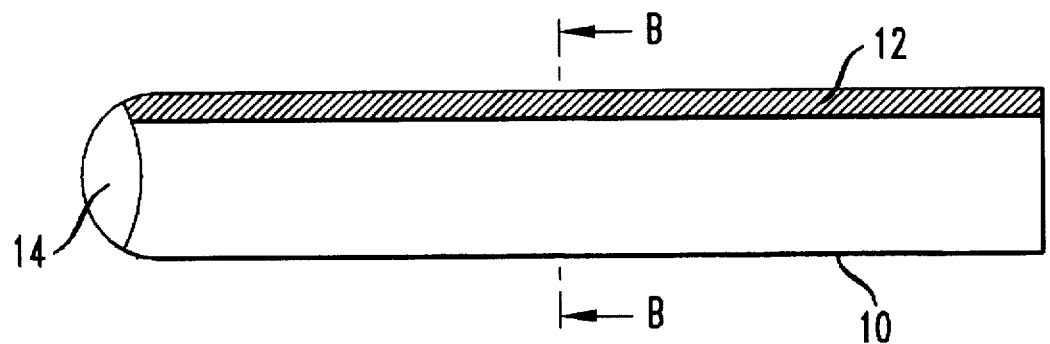
FIG. 1A illustrates a known open ended catheter.
Figure 1B:
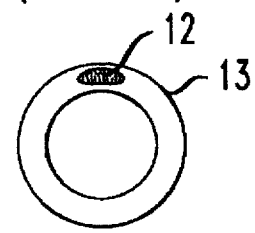
FIG. 1B illustrates a cross section of the known catheter illustrated in FIG. 1.
Figure 2:
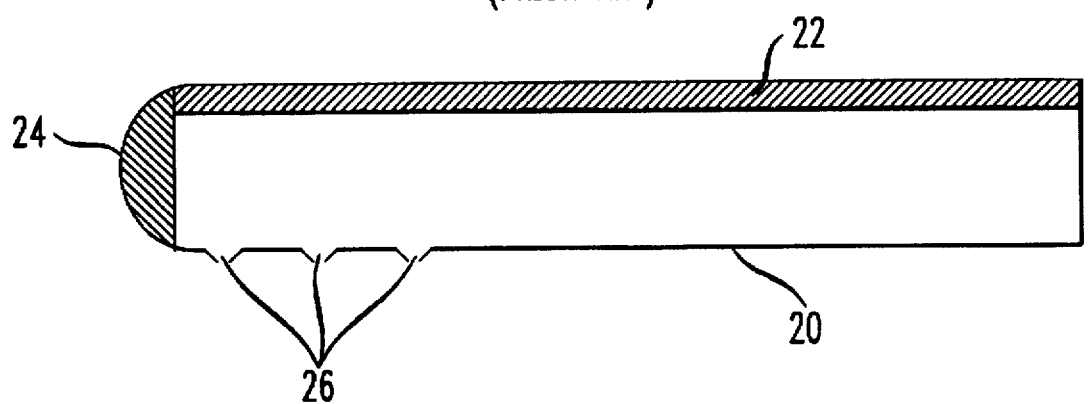
FIG. 2 illustrates a known Venous catheter including one way valves.
Figure 3A:
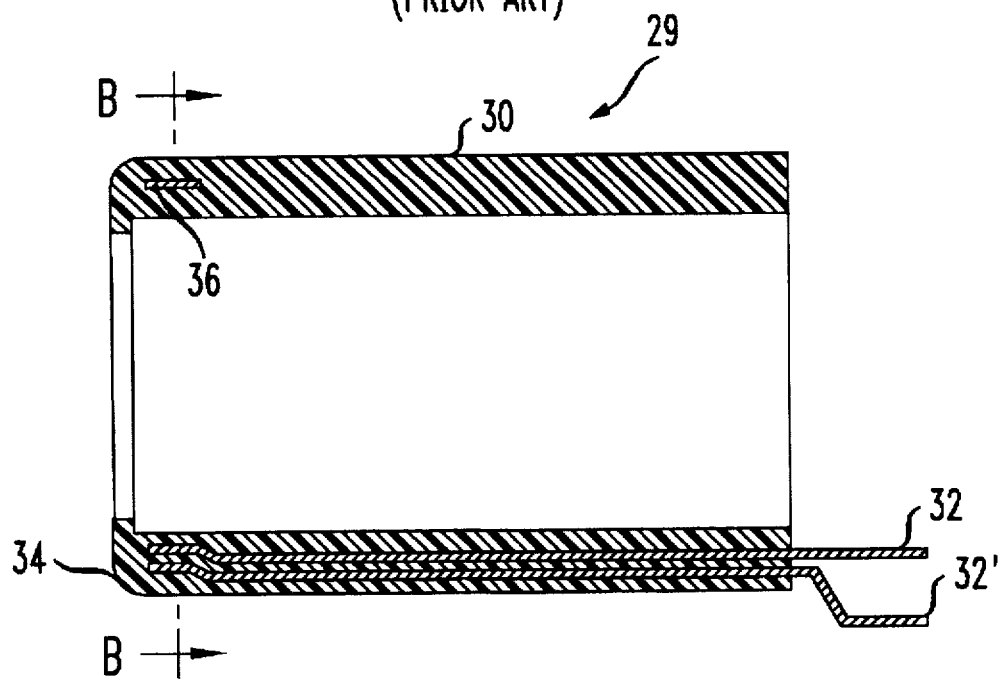
FIG. 3A illustrates a known catheter the location of which can be determined using a NMR imaging system.
Figure 3B:
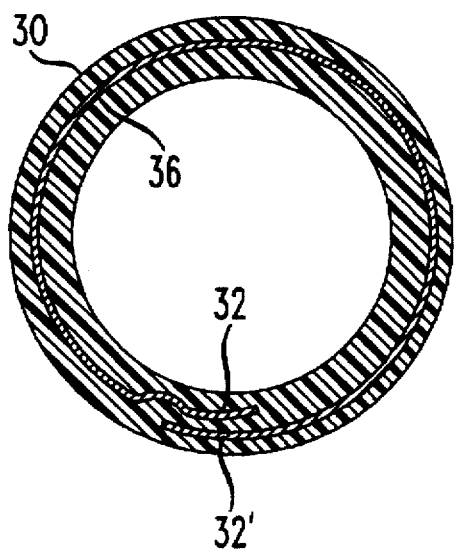
FIG. 3B illustrates a cross section of the known catheter illustrated in FIG. 3A.
Figure 4:
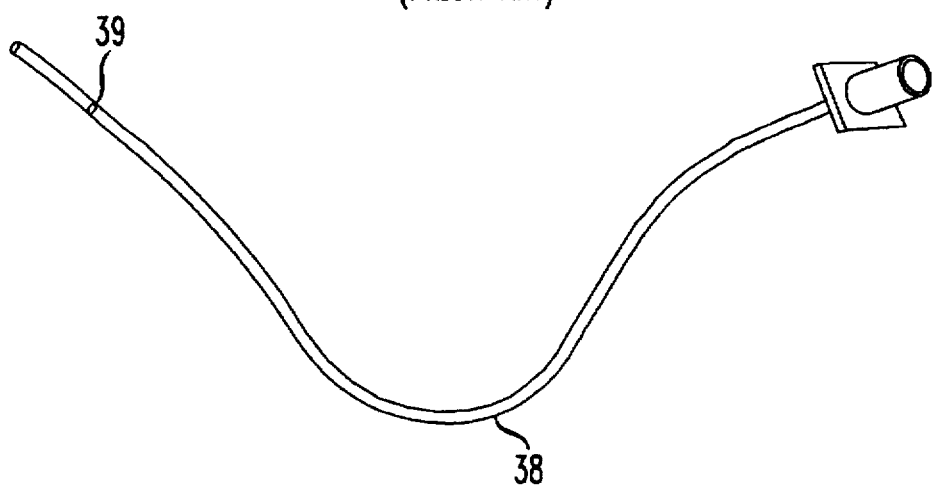
FIG. 4 illustrates a known catheter incorporating a bead of metallic foil near the tip of the catheter.
Figure 5:
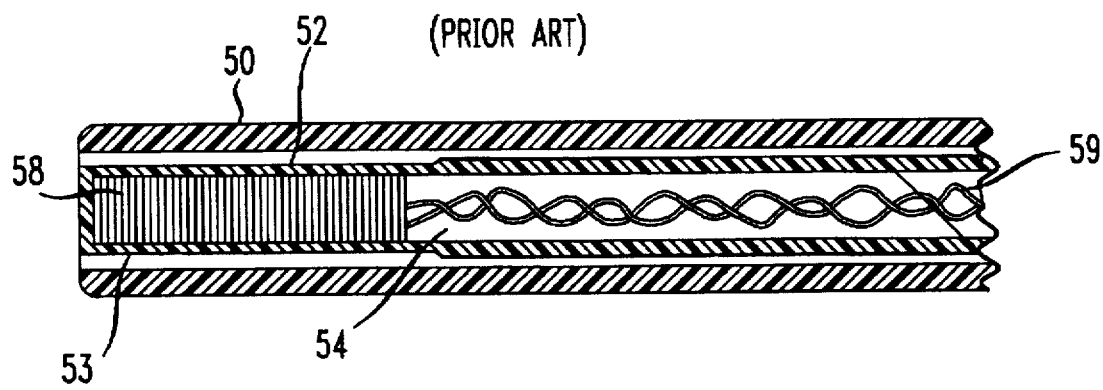
FIG. 5 illustrates a known catheter and removable detector inserted into the catheter.

Referring now to FIG. 6A, there is illustrated a closed end Venous catheter 60 implemented in accordance with one embodiment of the present invention.

As will be described below, an electromagnetic field detector device is incorporated directly into the catheter 60 of the present invention. In this manner, the detector device becomes an integral part of the catheter 60.

The incorporation of a detector device into the catheter 60, makes it suitable for use with a catheter locating apparatus which is the same as or similar to that described in U.S. Pat. No 4,905,698. Using such a catheter locating apparatus the location of the catheter 60 may be determined without the use of X-rays, e.g. Fluoroscopy.

Because the catheter design of the present invention, provides for the permanent presence of a detector device within the catheter 60, the location of the catheter 60 can be monitored at any time without the need for harmful X-rays. This is a significant advantage over the prior art system which uses a removable detector.

In addition to permitting the continuous or periodic monitoring of catheter location, the incorporation of the detector device directly into the catheter 60 overcomes many of the problems associated with the use of a removable detector device.

As will be discussed below, the catheter 60 will generally be more flexible than a catheter assembly incorporating a removable detector. This permits the catheter 60 of the present invention to be used for a variety of applications which the known catheter and removable detector are unsuitable for. In addition, since the detector device is incorporated into the catheter 60 the problems associated with removing the known removable detector device from a catheter, e.g., the possible breaking of the guide wire attached to the removable detector are avoided altogether.

The catheter 60 of the present invention comprises a catheter wall 62 made of a flexible polymer material. Imbedded into the catheter wall 62 is a pair of flexible conductive leads 64, 64', a strip of radio-opaque material 68, and a plurality of one way valves 66 which are designed to prevent the back flow of fluids, e.g., blood, into the catheter 60. The check valves 66 may be implemented as slits in the catheter wall 62.

As illustrated in FIG. 6A, the tip 72 of the catheter 60 includes a coil 70 of fine wire wrapped around a core 71. The cylindrical core 71 is made of a magnetically permeable material. In the illustrated embodiment, the coil 70 and the core 71 are incorporated, e.g., by a molding process, directly into the tip of the catheter 60. The leads 64, 64', coils 70 and core 71 form an electromagnetic field detection device. The coil 70 and leads 64, 64' may be made, e.g., of fine copper wire. When copper or aluminum wire is used, the magnetic susceptibility of the leads will be significantly different than that of the polymer material used to form the catheter wall 62.

In one embodiment, the polymer material used to form the wall 62 of the catheter 60 is also used to encapsulate the coil 70 and the core 71. To increase flexibility as compared to when a rigid core is used, the core 71 may be omitted or made of, e.g., a powdered magnetically permeable material. The coil 70 may be made of multiple layers of windings.

Referring now to FIG. 6B, there is illustrated a cross sectional view of the tip of the catheter 60 at the location indicated by the letter B in FIG. 6A. As illustrated in FIG. 6B, the tip of the catheter 60 comprises the cylindrical core 71, indicated by the cross hatched markings, which is surrounded by an inner layer of the wall 62, a loop of fine wire which is part of the coil 70, and an outer layer of the wall 62.

Referring now to FIG. 6c, there is illustrated a cross sectional view of another portion of the catheter 60 at the location indicated by the letter C in FIG. 6A As illustrated, at point C the catheter of the present invention includes conductive leads 64 and 64' and a segment of the radio opaque strip 68. In the illustrated embodiment, the leads 64 and 64' and radio-opaque strip are formed as integral components of the catheter wall 62. In addition, each of the leads 64, 64' and radio opaque strip 68 are completely surrounded by the polymer material of which the wall 62 is made.

As discussed above, the catheter 60 of the present invention includes a plurality of check valves 66. Referring now to FIG. 6D, there is illustrated a cross sectional view of the catheter 60 at location D. In FIG. 6D, the check valves 66 are shown in the closed position. In this position, the check valves 66 prevent the flow of blood into the lumen 69.

Referring now to FIG. 6E, there is illustrated a cross sectional view of the catheter 60 at location D when fluid is being injected into the tissue in which the catheter is placed. As illustrated by the arrows in FIG. 6E, the fluid passes out through the check valves 66 which open as a result of the fluid pressure inside the lumen 69.

The catheter 60 of the present invention overcomes many of the disadvantages of the prior art catheters. The incorporation of the electromagnetic detector components 70, 71, 64 and 64' permit the continuous or periodic monitoring of the catheter's location without the need for harmful X-rays. The incorporation of the radio-opaque strip 68 permits a permanent record to be made of the catheter's position, e.g., after insertion, using Fluoroscopy. Such a record may be important to serve as documentation which can be placed in a patient's file. In addition, the incorporation of check valves into the catheter 60 permits the injection of fluids into, e.g., veins, while avoiding the clotting problems and the need to use Heparin associated with catheters that do not incorporate such check valves.

Unlike the known removable detector system, the detector components 64, 64' 70, and 72 of the present invention are permanently incorporated into the catheter 60. Accordingly, they need not be designed to withstand the stress associated with withdrawing a detector from the center of a catheter. This permits the leads 64 and 64' to be made of very fine wire allowing for greater flexibility than is possible with the prior art system which uses a removable detector.

A catheter assembly 81 including an open end catheter 80 implemented in accordance with another embodiment of the present invention will now be described with reference to FIG. 7A.

As illustrated in FIG. 7A, the catheter assembly 81 includes the open ended catheter 80, a connecting tube 85, and an extension catheter 86. The connecting tube 85 is used to couple the open ended catheter 80 to the extension catheter 86 during use. As will be discussed below, the use of the extension catheter 86 provides a way of adjusting the overall length of the catheter assembly 81 to accommodate different patients.

To stabilize the extension catheter 86 in, e.g., body tissue, and to reduce the risk of infection a cuff 87 is attached to the outer surface of the extension catheter 86.

The open ended catheter 80 of the present invention illustrated in FIG. 7a comprises a catheter wall 82. Imbedded in the catheter wall 82 is a pair of flexible conductive leads 84, 84', a strip of radio opaque material 88, and markings 96 which are placed at fixed distances along the outer surface of the catheter 80. The catheter 80 is suitable for use, e.g., as an umbilical artery catheter, a feeding tube, a chest tube, and as an endotrachael tube.

As illustrated in FIG. 7A, the tip 92 of the catheter 80 opens onto the lumen 89 of the catheter 80. A coil 90 is incorporated into the tip of the catheter 80. In the illustrated open-ended catheter embodiment, a cylindrical core is not used. However, a hollow cylindrical core may be used if a sufficient opening is left in the center of the core to permit fluids and other material to pass between the lumen 89 of the catheter 80 and the opening in the catheter tip 92.

A cross section of the catheter 80 at location B is illustrated in FIG. 7B. As illustrated in FIG. 7B, the absence of a cylindrical core allows the center portion of the catheter 80 to remain open even at the tip 92. FIG. 7C illustrates a cross section of the catheter 80 at location C. As illustrated, at location C, the cross section of the catheter 80 is similar to that of catheter 70 at the same location.

Because the electromagnetic field detector components 84, 84' and 90 are integral components of the catheter 80, they do not occlude the lumen 89 as would a removable detector device. Furthermore, the catheter 80 offers advantages in terms of flexibility and the possibility of continuous positional monitoring not found in the prior art device which used a removable detector.

Accordingly, catheter 80 offers the advantages of permitting continuous or periodic monitoring of the catheter's location without the use of X-rays. In addition, it also permits the making of a permanent record of the catheter's location via the use of the radio-opaque strip 88.

Because the catheter 80 incorporates the coil 90 into the tip of the catheter 80, the overall length of the catheter 80 can not be readily adjusted by merely cutting off a portion of the catheter's distal end as commonly done with prior art open ended catheters. In accordance with the present invention, the portion of the proximal end of the catheter 80 which extends beyond the point the leads 84, 84' exit the catheter wall 82 is trimmed to adjust the overall length of the catheter assembly 81. In this manner, the overall length of the catheter assembly 81 can be easily adjusted without affecting the benefits of incorporating the coil into the distal end of the catheter 80.

Referring now to FIG. 8A, there is illustrated another open-ended catheter 91 implemented in accordance with another embodiment of the present invention. The caterer 91 includes many components which are the same as or similar to the components of the catheter 80. In FIGS. 7A and 8A like numbered elements refer to the same or similar components. The elements of the catheter 91 which are numbered the same as the elements of the catheter 80 will not be described again.

As illustrated in FIG. 8A, the catheter 91 includes a plurality of holes 93 in the side wall 82. In addition, a vent tube 95 is incorporated into the catheter 91. Referring now to FIG. 8B, there is illustrated a cross section of the catheter 91 at location C. As illustrated, the vent tube 95 is incorporated into the wall 82 of the catheter 91 along with the leads 84, 84'.

The vented catheter 91 is suitable for use, e.g., as a gastrointestinal catheter.

The catheter 91 offers the same advantages, in terms of permitting the continuous or periodic monitoring of the catheter's position without the need for X-rays as does the other catheters of the present invention.

The catheters illustrated in FIGS. 7A, 8A, and 9A, of the present invention are intended as illustrations of exemplary embodiments. It will be apparent to one of ordinary skill in the art that the features of the present invention may be used to provide catheters suitable for a wide range of applications.

What is claimed is:

1. A closed end catheter device, comprising:

a tubular wall having a proximal end and a closed distal end;

a pair of conductive leads incorporated into the tubular wall, the pair of leads protruding near the proximal end and extending towards the distal end;

a coil of wire incorporated into the distal end of the tubular wall, the coil of wire being coupled to the pair of leads and comprising a plurality of circular conductive windings; and a solid core of magnetically permeable material located within the coil of wire.

2. The catheter device of claim 1, further comprising:

an extension catheter; and means for coupling the extension catheter to the proximal end of the tubular wall.

3. The catheter device of claim 2 wherein the extension catheter further comprises a cuff for stabilizing the extension catheter in biological tissue.

4. The catheter device of claim 3, wherein the extension catheter includes a distal end and a proximal end, the distal end of the extension catheter being coupled to the proximal end of the tubular wall, the cuff being located near the distal end of the extension catheter.

5. The catheter of claim 4, wherein the extension catheter is made of a polymer material and includes a strip of radio-opaque material.

6. A closed end venous catheter, comprising:

a tubular wall made of a polymer material having a proximal end and a closed distal end;

a pair of conductive leads incorporated into the tubular wall, the pair of conductive leads protruding near the proximal end and extending towards the closed distal end;

a coil of wire incorporated into the closed distal end of the tubular wall, the coil of wire being coupled to the pair of leads and comprising a plurality of circular conductive windings;

a plurality of one way valves located in the tubular wall near the closed distal end;

a solid core of magnetically permeable material located within the coil of wire; and a radio opaque strip incorporated into the tubular wall and extending along the length thereof.

7. A catheter device, comprising:

a tubular wall having a proximal end and a distal end;

a pair of conductive leads incorporated into the tubular wall, the pair of leads protruding near the proximal end and extending towards the distal end;

a coil of wire incorporated into the distal end of the tubular wall, the coil of wire being coupled to the pair of leads and comprising a plurality of circular conductive windings; and a radio opaque strip incorporated into the tubular wall and extending along the length thereof.

8. The catheter device of claim 7, further comprising:

a solid core of magnetically permeable material located within the coil of wire.

9. The catheter device of claim 8, further comprising:

a plurality of one way valves located in the tubular wall near the distal end.

10. The catheter device of claim 9, wherein the catheter is a closed end venous catheter and wherein the core of magnetically permeable material is made of a powdered material.

11. The catheter device of claim 7, wherein the catheter is an open ended catheter and wherein the tubular wall includes a plurality of markings located at fixed intervals on an exterior surface of the tubular wall.

12. The catheter device of claim 11, further comprising:

a hollow cylindrical core of magnetically permeable material located within the coil of wire.

13. The catheter device of claim 11, wherein the tubular wall further includes:

a plurality of openings near the distal end of the tubular wall.

14. The catheter device of claim 13, wherein the tubular wall further comprises:

a vent tube extending from the distal end to the proximal end.

15. The catheter device of claim 14, further comprising a hollow cylindrical core of magnetically permeable material located within the coil of wire.

16. The catheter device of claim 15, wherein the leads include fine copper wire.

17. The catheter device of claim 16, wherein the leads include fine aluminum wire.

* * * * *